United States Patent [19]

Krespan

[11] Patent Number: 5,235,069
[45] Date of Patent: Aug. 10, 1993

[54] PROCESS FOR THE PREPARATION OF DIFLUOROMALEIC ANHYDRIDE AND INTERMEDIATE COMPOUNDS PRODUCED THEREBY

[75] Inventor: Carl G. Krespan, Wilmington, Del.

[73] Assignee: E. I. Du Pont de Nemours and Company, Wilmington, Del.

[21] Appl. No.: 746,098

[22] Filed: Feb. 14, 1991

Related U.S. Application Data

[62] Division of Ser. No. 436,466, Nov. 14, 1989, Pat. No. 5,112,993.

[51] Int. Cl.$^5$ .......................................... C07D 333/32
[52] U.S. Cl. .......................................... 549/62
[58] Field of Search .......................................... 549/62

[56] References Cited

U.S. PATENT DOCUMENTS

| | | | |
|---|---|---|---|
| 2,891,968 | 6/1959 | Raash | 549/254 |
| 3,069,431 | 12/1962 | Krespan | 549/82 |
| 3,485,827 | 12/1969 | Fried | 540/60 |
| 3,485,829 | 12/1969 | Fried | 540/60 |
| 3,761,453 | 9/1973 | Jones | 528/70 |
| 3,792,022 | 2/1974 | Jones | 526/242 |
| 4,111,879 | 9/1978 | Mori et al. | 523/122 |

OTHER PUBLICATIONS

C. Krespan et al., *J. Org. Chem.*, "Fluorosulfonation" 51 (23) pp. 4460–4466 (1986).
W. J. Feast, et al., *J. Chem. Soc.* (C), "Fluorination of Perchloro-2,5-dihydrofuran," pp. 769–772 (1971).
H. Scharf et al., *Chemical Abstracts*, 80: 107506y, p. 333, abstract of *Z. Naturforsch., Teil B* 1973, 28 (9–10), pp. 662–681, (1974).
H. Scharf et al. *Chem. Ber.*, 106, pp. 1707–1708 (1973).
H. Scharf et al., *Z. Naturforsch, Teil B*, 28 (9–10) pp. 662–681 (1973).

*Primary Examiner*—Mark Russell

[57] ABSTRACT

A process for producing difluoromaleic anhydride by reacting sulfur trioxide with a fluorinated precursor selected from the group consisting of hexafluoro-2,5-dihydrofuran, hexafluoro-2,5-dihydrothiophene, difluoro-2,5-dihydrothiophene-2,5-dione and tetrafluoro-2,5-dihydrothiophene-2-one. Also disclosed are the compounds difluoro-2,5-dihydrothiophene-2,5-dione and tetrafluoro-2,5-dihydrothiophene-2-one.

1 Claim, No Drawings

PROCESS FOR THE PREPARATION OF DIFLUOROMALEIC ANHYDRIDE AND INTERMEDIATE COMPOUNDS PRODUCED THEREBY

CROSS REFERENCE TO RELATED APPLICATION

This application is a division of application Ser. No. 07/436,466 filed on Nov. 14, 1989 now U.S. Pat. No. 5,112,993.

FIELD OF INVENTION

The present invention relates to a process for the preparation of difluoromaleic anhydride. More particularly, this invention relates to reacting sulfur trioxide with certain fluorinated precursors to produce difluoromaleic anhydride or intermediates thereof.

BACKGROUND OF THE INVENTION

U S. Pat. No. 2,891,968 describes the preparation of difluoromaleic anhydride by the dehydration of difluoromaleic acid, which in turn is obtained by the dehydrofluorination of trifluorosuccinic acid. The present invention represents an improvement over this preparation with respect to ease of synthesis of the difluoromaleic anhydride.

L. S. Kobrina, et. al., Zh. Org. Khim., vol. 8, pp. 2165-2167 (1972) obtained difluoromaleic acid (which can be converted to the anhydride, see U.S. Pat. No. 2,891,968, supra) in 54% yield by treatment of pentafluorophenol with peroxyacetic acid. Difluoromaleic acid was also obtained by analogous reactions of tetrafluoro-p- or tetrafluoro-o-benzoquinone, tetrafluoropyrocatechol and tetrafluoro-muconic acid. However, the preparation of this reference requires the oxidation of a fluorophenol, which is not necessary to the present procedure.

C. G. Krespan and D. A. Dixon, J. Org. Chem., vol. 51, pp. 4460-4466 (1986) describe the reaction of $SO_3$ with perfluoro-2-butene. In this reaction only one of the terminal carbons reacted to form a carbonyl group, yielding the compound $CF_3CF=CFCO_2SO_2F$ in relatively low yields even though high reaction temperatures and long reaction times were used. A small amount (0.05%) of trimethyl borate was present as a stabilizer in the $SO_3$ used. The use of boron compounds as catalysts is discussed in this paper. However, neither difluoromaleic anhydride nor difluoromaleic acid are produced in the reviewed reactions.

Difluoromaleic anhydride is useful for the capping of polyimide prepolymers and polymers (U.S. Pat. No. 4,173,700), as a "cure site" monomer in fluoropolymers (U.S. Pat. Nos. 3,792,022 and 3,761,453) and as a comonomer with phenyl vinyl ether to form an alternating copolymer (G. Canessa C., Bol. Soc. Chil. Quim., vol. 26, pp. 25-37). In German Patent 2,649,743 it is used as a component of an antifouling coating. It is used as a chemical intermediate in the preparation of biologically active compounds in U.S. Pat. Nos. 3,485,829 and 3,485,827.

It is an object of the present invention to provide a one step process for the production of difluoromaleic anhydride from commonly available starting materials. A feature of the present invention is the production of useful intermediate compounds. It is an advantage of the present invention to provide catalysts for the reaction to facilitate commercial scale production of difluoromaleic anhydride. These and other objects, features and advantages of the present invention will become apparent upon having reference to the following description of the invention.

SUMMARY OF THE INVENTION

A process for the production of difluoromaleic anhydride is provided, comprising reacting sulfur trioxide with a fluorinated precursor selected from the group consisting of hexafluoro-2,5-dihydrofuran, hexafluoro-2,5-dihydrothiophene, difluoro-2,5-dihydrothiophene-2,5-dione and tetrafluoro-2,5-dihydrothiophene-2-one. Usually at least about 3 moles of sulfur trioxide is used for each mole of fluorinated precursor used. The reaction may optionally be catalyzed by trivalent boron compounds. Also provided are the compounds difluoro-2,5-dihydrothiophene-2,5-dione and tetrafluoro-2,5-dihydrothiophene-2-one which are useful as intermediates in the production of difluoromaleic anhydride.

DETAILS OF THE INVENTION

Difluoromaleic anhydride is prepared by the reaction of sulfur trioxide ($SO_3$) with a fluorinated precursor selected from the group consisting of hexafluoro-2,5-dihydrofuran, hexafluoro-2,5-dihydrothiophene, difluoro-2,5-dihydrothiophene-2,5-dione and tetrafluoro-2,5-dihydrothiophene-2-one. The sulfur trioxide is preferably present as $SO_3$ alone, or it may be present in solution in sulfuric acid, commonly known as oleum. Usually at least about 3 moles of $SO_3$ are present for each mole of fluorinated precursor. Although no upper limit on the molar ratio of $SO_3$ to fluorinated precursor is known, molar ratios of $SO_3$ to fluorinated precursor of about 3 to about 10 are preferred.

Hexafluoro-2,5-dihydrofuran can be prepared by the method of W. J. Feast, et. al., J. Chem. Soc. C, vol. 1971, pp. 769-772. U.S. Pat. No. 3,069,431 reports a method for the synthesis of hexafluoro-2,5-dihydrothiophene. The precursor for the thiophene, hexafluorocyclobutene, is commercially available.

Both difluoro-2,5-dihydrothiophene-2,5-dione and tetrafluoro-2,5-dihydrothiophene-2-one are made by the reaction of $SO_3$ with hexafluoro-2,5-dihyrothiophene (Example 3, infra). Thus reaction of the hexafluoro-2,5-dihydrothiophene with $SO_3$ under reaction conditions less vigorous than those reported herein that produce difluoromaleic anhydride will produce difluoro-2,5-dihydrothiophene-2,5-dione and/or tetrafluoro-2,5-dihydrothiophene-2-one. Less vigorous conditions include one or more of lower reaction temperatures, shorter reaction times, lesser amounts of $SO_3$ and the absence of catalysts. Since difluoro-2,5-dihydrothiophene-2,5-dione and tetrafluoro-2,5-dihydrothiophene-2-one are both intermediates in the reaction of hexafluoro-2,5-dihydrothiophene with $SO_3$ to produce difluoromaleic anhydride, reaction of either difluoro-2,5-dihydrothiophene-2,5-dione or tetrafluoro-2,5-dihydrothiophene-2-one with $SO_3$ under conditions described herein will yield difluoromaleic anhydride.

Compounds containing trivalent boron may optionally be added as catalysts to accelerate the formation of difluoromaleic anhydride. They are especially useful at relatively low reaction temperatures. Active catalysts include, but are not limited to trimethyl borate, boron trifluoride, boric oxide and boron trichloride. The amount of boron catalyst used is preferably about 0.5 to about 5 weight percent of the $SO_3$ present.

The reaction to produce difluoromaleic anhydride is run at 25°–200° C., preferably 50°–100° C. Reaction times typically vary from about 0.5–24 hr., the longer times being needed at lower temperatures. Reactions may be run at atmospheric pressure, but to achieve higher reaction temperatures, the reaction can be run under pressure, typically up to about 20 atm. A solvent inert to the starting materials and products may be present, but it is preferred to conduct the reaction in the absence of solvent. Water should be excluded to a reasonable extent, thus starting materials should be dry and moist air should be excluded from the reaction.

Reaction vessels should be inert to the starting materials and products. Glass and alloys such as stainless steel and Hastelloy ®, a trademark of Stoody Deloro Stellite, Inc., are suitable for reaction vessels.

Products may be isolated by standard methods known to those skilled in the art such as distillation and crystallization. Such methods are illustrated in the Examples.

EXAMPLE 1

Preparation of Difluoromaleic Anhydride from Hexafluoro-2,5-dihydrofuran

Sulfur trioxide (336 g, 4.2 mol) was stirred at 25° C. while 83 g (0.47 mol) of hexafluoro-2,5-dihydrofuran was distilled in. No interaction was apparent while the temperature dropped to 15° C. and the $SO_3$ solidified. Addition of 1 g of trimethyl borate initiated reaction, which was allowed to progress overnight. Then another 42 g (0.24 mol) of hexafluoro-2,5-dihydrofuran was added, and the mixture was refluxed for 12 hr. while the temperature rose to 92° C. Distillation afforded, after a large foreshot, 69.0 g (74%) of crude difluoromaleic anhydride, bp 100°–125° C. Redistillation gave 50.0 g (53%) of difluoromaleic anhydride, bp 125°–126° C. IR (1% in $CHCl_3$): 1880 (w), 1815 (s) and 1760 (m) (C=O, C=C), 1290 and 1185 $cm^{-1}$ (C-F) NMR (acetone-$d_6$): $^{19}F\phi - 141.2$ (s,=CF). UV: $\epsilon$ isooctane/235 nm 3176.

Confirmation of the structure was obtained when the anilide was prepared by adding 2.9 g (0.022 mol) of difluoromaleic anhydride to a solution of 1.9 g (0.020 mol) of aniline in 100 ml of ether. The mixture was stirred for 15 min., filtered, and the filter cake dried to give 4.0 g (88%) of anilide, mp 192°–193° C. (literature mp 193°–195° C.). NMR (acetone-$d_6$): $^{19}F\phi$-124.9 (m, 1F,=CF), −132.8 (d, $J_{FF}$4.7 Hz, 1F, (=CF).

EXAMPLE 2

Preparation of Difluoromaleic Anhydride from Hexafluoro-2,5-dihydrothiophene

Commercial sulfur trioxide (176 g, 2.20 mol) was treated cautiously with 2.0 g of trimethyl borate, and the mixture was stirred while 72.9 g (0.38 mol) of hexafluoro-2,5-dihydrothiophene was added over 30 min. A mildly exothermic reaction caused reflux. The mixture was stirred 1 hr. while the temperature came down and then was heated to 60° C. where a second exotherm was accompanied with pronounced gassing. A sample of the off-gases was shown by IR to be $SO_2$ with a minor amount of $FSO_2OSO_2F$ present. Reaction was continued at 60°–65° C. until gas evolution subsided, then at reflux for 2 hr. while the pot temperature fell from 90° C. to 80° C. Distillation gave a large foreshot, bp 40°–100° C. followed by 37.0 g (73%) of crude difluoromaleic anhydride, bp 100°–125° C. nearly pure by GC. The IR spectrum was substantially the same as that of a known sample.

EXAMPLE 3

Preparation of Tetrafluoro-2,5-dihydrothiophene-2-one and Difluoro-2,5-dihydrothiophene-2,5-dione Sulfur trioxide (128.0 g, 1.60 mol) was added rapidly to 77.6 g (0.40 mol) of hexafluoro-2,5-dihydrothiophene. After an initial exotherm, the mixture was refluxed for 30 min. and fractionated to give 121.9 g, bp 42°–55° C., shown to be mainly pyrosulfuryl fluoride by $^{19}F$ NMR, and 29.5 g of crude tetrafluoro-2,5-dihydrothiophene, bp 77°–85° C. Redistillation of this product afforded 16.9 g (25%) of tetrafluoro-2,5-dihydrothiophene-2-one, bp 83° C. IR ($CCl_4$): 1755 (C=O) and 1740 $cm^{-1}$(C=C). NMR ($CCl_4$): $^{19}F\phi - 92.0$ (d of d, $J_{FF}$14.7, 5.5 Hz, 2F, $CF_2$), −133.5 (q, $J_{FF}$14.3 Hz, 1F, CF), −144.3 (d of t, $J_{FF}$13.9, 5.5 Hz, 1F, CF). MS: m/e 171.9615 (M+; calcd for $C_4F_4OS$, 171.9606), 143 9664 (M+—CO; cald, 143,9657), 121.9641 (M+—$CF_2$; calcd, 121.9638). Anal. Calcd for $C_4F_4OS$: C, 27.91; S, 18.63 Found: C, 28.27; S, 19.16.

Further distillation of the reaction mixture afforded 32.6 g of crude difluoro-2,5-dihydrothiophene-2,5-dione bp 80°–86° C. (100 mm), which solidified on standing. Recrystallization from hexane/ether followed by sublimation at 45°–50° C. (10 mm) gave 12.7 g of nearly colorless difluoro-2,5-dihydrothiophene-2,5-dione, mp 57°–58° C. Evaporation of the filtrate and sublimation at 40° C. (10 mm) gave an additional 4.7 g of difluoro-2,5-dihydrothiophene-2,5-dione, mp 52°–56° C., for a total yield of 17.4 g (29%). An analytical sample, mp 58°–59° C., was prepared by sublimation at 30° C. (10 mm). IR ($CCl_4$); 1760 (w) and 1715 (s) $cm^{-1}$(C=O and C=C). NMR ($CCl_4$): $^{19}F\phi - 132.2$ (s, CF). Anal. Calcd for $C_4F_2O_2S$: C, 32.00; S, 21.36. Found: C, 32.81; S, 21.64.

Although preferred embodiments of the invention have been described hereinabove, it is to be understood that there is no attempt to limit the invention to the precise constructions herein disclosed, and it is to be further understood that the right is reserved to all changes coming within the scope of the invention as defined by the appended claims.

What is claimed is:

1. The compound tetrafluoro-2,5-dihydrothiophene-2-one.

* * * * *